US006264687B1

(12) United States Patent
Tomonto

(10) Patent No.: US 6,264,687 B1
(45) Date of Patent: Jul. 24, 2001

(54) MULTI-LAMINATE STENT HAVING SUPERELASTIC ARTICULATED SECTIONS

(75) Inventor: Charles V. Tomonto, Neshanic Station, NJ (US)

(73) Assignee: Cordis Corporation, Miami, FL (US)

( * ) Notice: Subject to any disclaimer, the term of this patent is extended or adjusted under 35 U.S.C. 154(b) by 0 days.

(21) Appl. No.: 09/287,036

(22) Filed: Apr. 6, 1999

Related U.S. Application Data
(60) Provisional application No. 60/082,397, filed on Apr. 20, 1998.

(51) Int. Cl.[7] ........................................................ A61F 2/06
(52) U.S. Cl. ............................................................ 623/1.16
(58) Field of Search ................................. 623/1.13, 1.15, 623/1.16, 1.44, 1.46

(56) References Cited

U.S. PATENT DOCUMENTS

| | | | |
|---|---|---|---|
| 4,403,612 | 9/1983 | Fogarty | 128/344 |
| 4,665,905 | 5/1987 | Brown | 128/80 |
| 4,733,665 | 3/1988 | Palmaz | 128/343 |
| 4,925,445 | 5/1990 | Sakamoto | 604/95 |
| 5,019,090 | 5/1991 | Pinchuk | 606/194 |
| 5,195,984 | 3/1993 | Schatz | 606/195 |
| 5,304,197 | 4/1994 | Pinchuk | 606/194 |
| 5,383,928 | 1/1995 | Scott | 623/1 |
| 5,480,423 | 1/1996 | Ravenscoft | 623/1 |
| 5,507,771 | 4/1996 | Gianturco | 606/198 |
| 5,554,181 | 9/1996 | Das | 623/1 |
| 5,662,675 | * 9/1997 | Stockert et al. | 606/195 |
| 5,858,566 | 1/1999 | Zhang | 428/694 |
| 5,928,279 | * 7/1999 | Shannon et al. | 623/1.44 |
| 5,980,552 | * 11/1999 | Pinchasik et al. | 606/198 |
| 6,001,125 | * 12/1999 | Golds et al. | 623/1.44 |
| 6,056,776 | * 5/2000 | Lau et al. | 623/1.16 |
| 6,099,561 | * 8/2000 | Alt | 623/1.44 |
| 6,129,755 | * 10/2000 | Mathis et al. | 623/1.15 |

FOREIGN PATENT DOCUMENTS

| | | | | |
|---|---|---|---|---|
| A1 0 335 341 | * 3/1989 | (EP) | | 623/1.16 |
| 553 960 | 1/1993 | (EP) | | A61F/2/06 |
| 606 165 | 1/1994 | (EP) | | A61F/2/06 |
| 689 805 | 6/1995 | (EP) | | A61F/2/06 |
| 806190 | 5/1997 | (EP) | | A61F/2/06 |

* cited by examiner

*Primary Examiner*—David H. Willse
*Assistant Examiner*—Suzette J. Jackson

(57) ABSTRACT

In accordance with the present invention, there is provided a stent for implantation into a vessel of a patient. The stent has at least two plastically deformable and expandable tubular graft members for expansion within a vessel. Each of the graft member has a first end, a second end, a wall section disposed therebetween and a lumen extending therethrough. The stent further includes at least one articulation connecting the first end of one of the graft members with the second end of the other graft member. Wherein the articulation is made from a superelastic material.

11 Claims, 3 Drawing Sheets

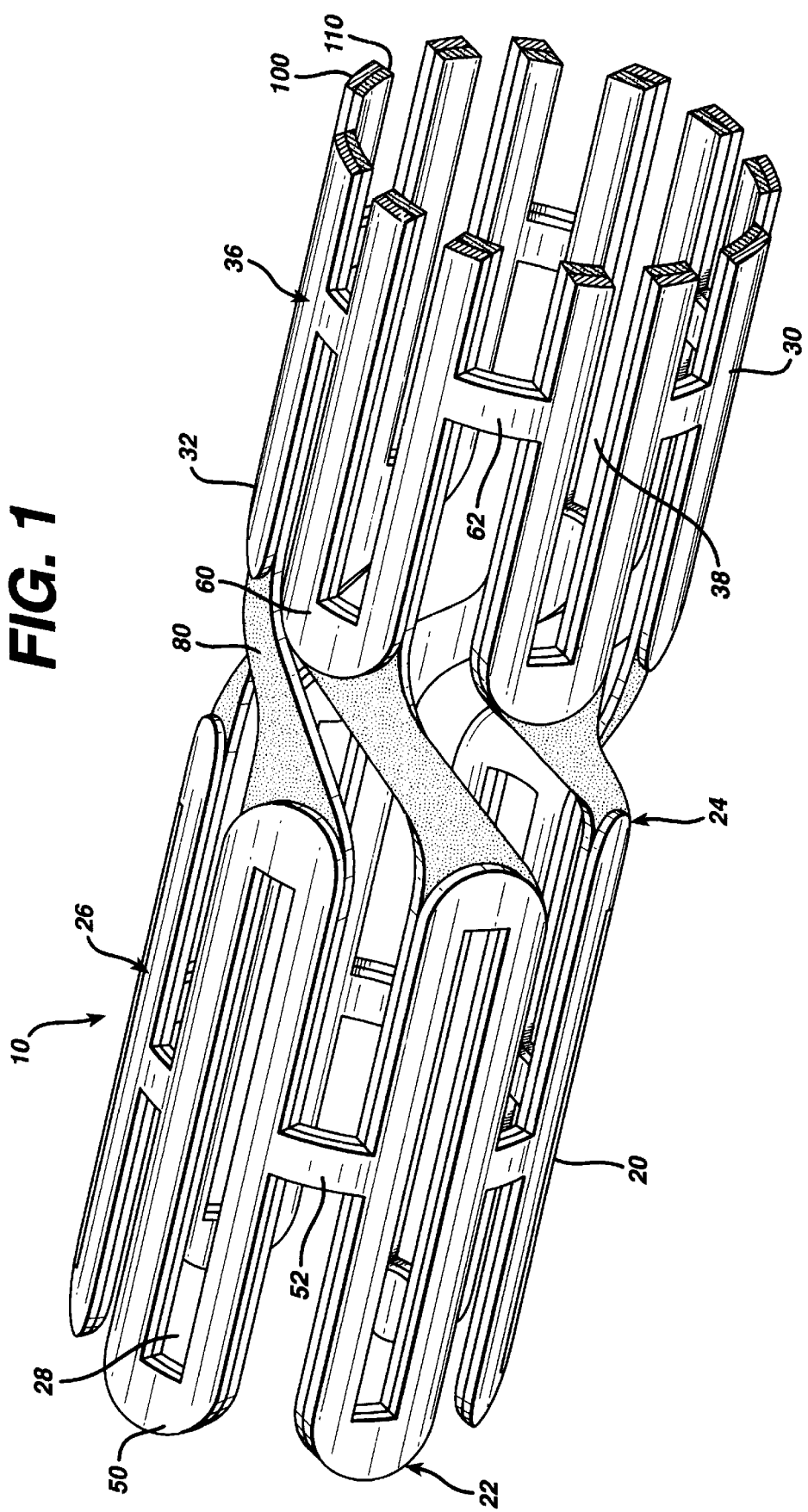

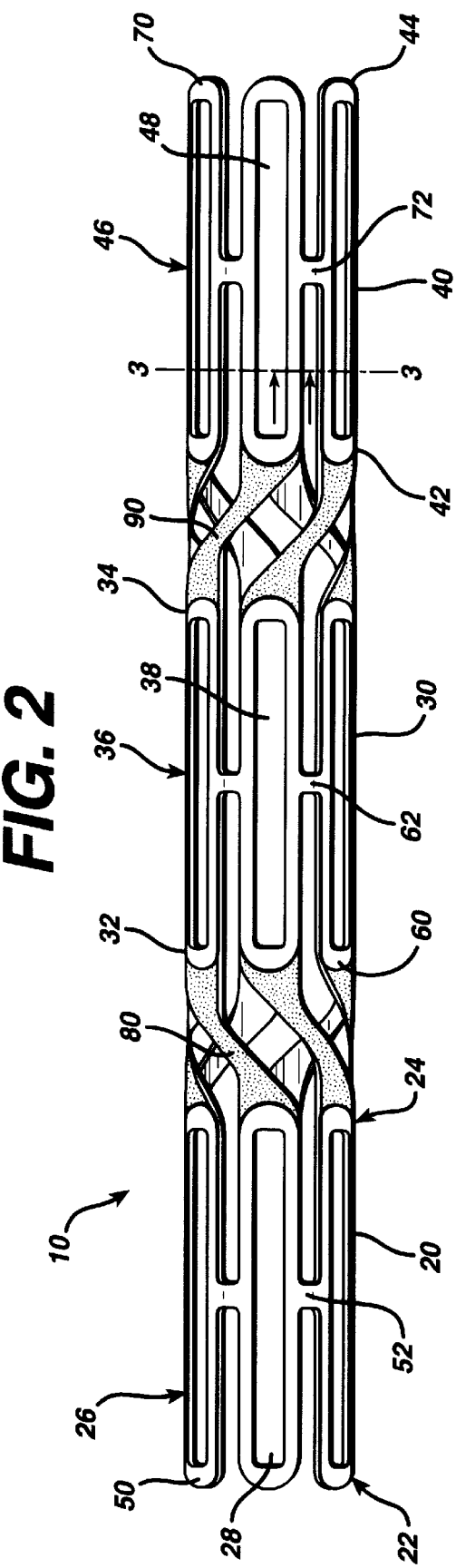

MULTI-LAMINATE STENT HAVING SUPERELASTIC ARTICULATED SECTIONS

This application claims benefit of provisional application Ser. No. 60/082,397 filed Apr. 20, 1998.

FIELD OF THE INVENTION

The present invention relates to an expandable intraluminal graft for use within a body passageway or duct and, more particularly, expandable intraluminal vascular grafts which are particularly useful for repairing blood vessels narrowed or occluded by diseased luminal grafts.

BACKGROUND OF THE INVENTION

Intraluminal endovascular grafting or stenting has been demonstrated to be an effective alternative to conventional vascular surgery. Intraluminal endovascular grafting involves the percutaneous insertion into a blood vessel of a tubular prosthetic graft or stent and its delivery via a catheter to the desired location within the vascular system. Advantages of this method over conventional vascular surgery include obviating the need for surgically exposing, incising, removing, replacing, or bypassing the defective blood vessel.

Structures which have previously been used as intraluminal vascular grafts have included various types of stents which are expanded within a vessel by a balloon catheter such as the one described in U.S. Pat. No. 5,304,197 issued to Pinchuk et al. on Apr. 19, 1994, which is hereby incorporated herein by reference. Examples of different types of stents include helical wound wires such as those described in U.S. Pat. No. 5,019,090 issued to Pinchuk on May 28, 1991, which is hereby incorporated herein by reference, and stents formed by cutting slots into a metal tube, such as the one described in U.S. Pat. No. 4,733,665 issued to Palmaz on Mar. 29, 1988, which is hereby incorporated herein by reference.

Other types of stents include self expanding stents, typically made from a superelastic material, such as a nickel titanium alloy (Nitinol). The prior art makes reference to the use of Nitinol, which has shape memory and/or superelastic characteristics, in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its, original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable (the Af temperature). The shape of the metal during this heat treatment is the shape "remembered." The heat treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape if unrestrained. If restrained, the metal will remain martensitic until the restraint is removed.

Methods of using the shape memory characteristics of these alloys in medical devices intended to be placed within a patient's body present operational difficulties. For example, with shape memory alloys having a stable martensite temperature below body temperature, it is frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices can be introduced into a patient's body with little or no problem, but they must be heated to the martensite-to-austenite transformation temperature which is frequently high enough to cause tissue damage and very high levels of pain.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

However, in general, the foregoing structures, both balloon expandable and self-expanding, have one major disadvantage in common. Insofar as these structures must be delivered to the desired location within a given body passageway in a collapsed state, in order to pass through the body passageway. While it is necessary for the expanded stent to have enough rigidity to maintain the integrity of the vessel it is implanted into, it also needs to have sufficient flexibility so that it can be navigated through tortuous vessels. For repairing blood vessels narrowed or occluded by disease, or repairing other body passageways, the length of the body passageway which requires repair, as by the insertion of a stent, may present problems if the length of the required graft cannot negotiate the curves or bends of the body passageway through which the graft is passed by the catheter. In other words, in many instances, it is necessary to support a length of tissue within a body passageway by a graft, wherein the length of the required graft exceeds the length of a graft which can be readily delivered via a catheter to the desired location within the vascular system. Some grafts do not have the requisite ability to bend so as to negotiate the curves and bends present within the vascular system, particularly prostheses or grafts which are relatively rigid and resist bending with respect to their longitudinal axes.

Accordingly, one solution to this problem has been the development of an articulated stent. An example of an articulated stent is given in U.S. Pat. No. 5,195,984 issued to Schatz on Mar. 23, 1993, which is hereby incorporated herein by reference. Such a stent is particularly useful for critical body passageways, such as the left main coronary artery of a patient's heart. Schatz discloses a stent having a plurality of expandable and deformable individual intraluminal vascular grafts or stents wherein and adjacent grafts are flexibly connected by a single connector members.

Recently, however, there has been a need to improve upon the stent disclosed in the Schatz reference. Specifically, it has been a desire to the technical community to make such a stent which is even more flexible, so that the stent can navigate tortuous vessels better than before. The present invention provides such a stent.

SUMMARY OF THE INVENTION

In accordance with the present invention, there is provided a stent for implantation into a vessel of a patient. The stent has at least two plastically deformable and expandable tubular graft members for expansion within a vessel. Each of the graft member has a first end, a second end, a wall section disposed therebetween and a lumen extending therethrough. The stent further includes at least one articulation connecting the first end of one of the graft members with the second end of the other graft member. Wherein the articulation is made from a superelastic material.

BRIEF DESCRIPTION OF DRAWINGS

The foregoing and other aspects of the present invention will best be appreciated with reference to the detailed description of the invention in conjunction with the accompanying drawings, wherein:

FIG. 1 is a partial perspective view of a stent made in accordance with the present invention.

FIG. 2 is a side view of a stent made in accordance with the present invention.

FIG. 3 is a partial cross sectional view of the stent shown in FIG. 2 taken along line 3—3.

DETAILED DESCRIPTION OF THE INVENTION

Figure 4:
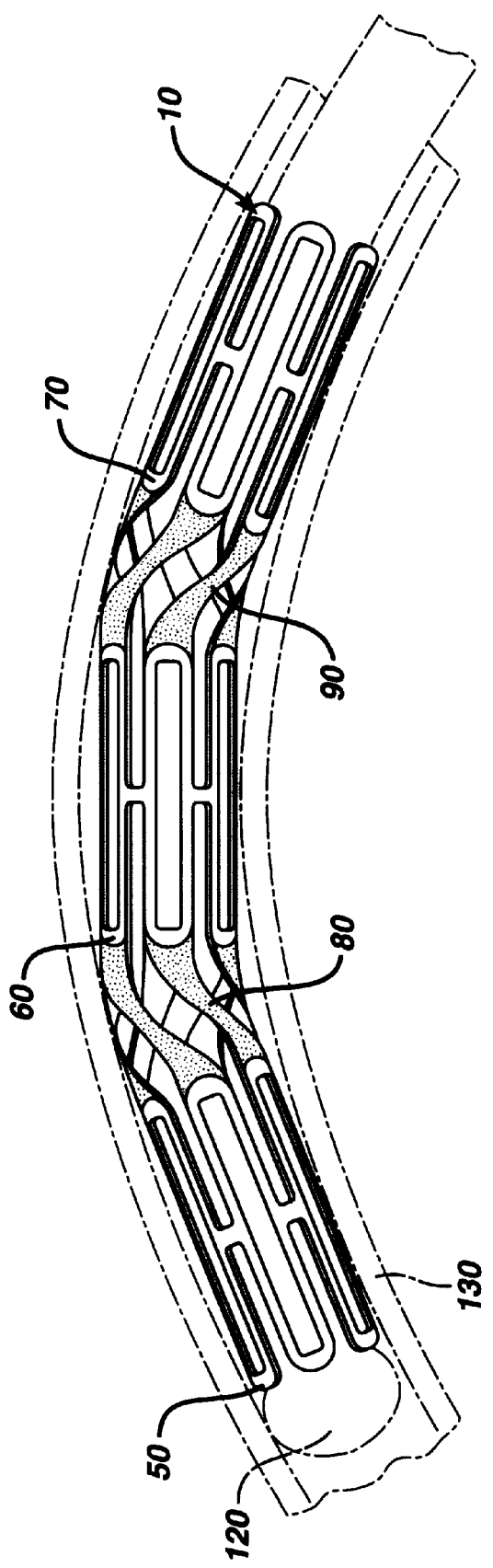
FIG. 4 is a view similar to that of FIG. 2 but showing the stent as it would appear when navigating a body vessel.

Referring now to the drawings in detail wherein like numerals indicate the same element throughout the views, there is shown in FIGS. 1 and 2 a stent 10 made in accordance with the present invention. Stent 10 is shown in its collapsed condition ready to be disposed on a balloon catheter for delivery and subsequent deployment into a vessel of a patient. Stent 10 includes at least two expandable grafts. Stent 10 is shown as having three expandable grafts 20, 30 and 40 each having a first end, 22, 32 and 42, and a second end, 24, 34 and 44, and a wall surface, 26, 36 and 46, disposed therebetween. The wall surface has a plurality of slots, for example 28, 38 and 48, formed therein. The grafts are formed from a metal tube and the slots are cut therein, typically by laser cutting or photochemical processing. After the slots are cut therein, each graft comprises a plurality of loops 50, 60 and 70, wherein adjacent loops are connected by at least one strut 52, 62 and 72.

Grafts 20 and 30 and 40 are connected together by at least one articulation 80, and grafts 30 and 40 are connected together by at least one articulation 90. As seen from the figures, the articulations connect a loop from one graft to a loop from another graft. However, it is preferable that the articulation does not connect one loop of one stent to a loop of another stent directly across it. In stead it connects the loops along a curved path which is angled with respect to the longitudinal axis of the stent running through the lumen.

The particular design of the present stent and its advantages are best understood by describing the materials the stent is made from and how the slots and articulations are cut therefrom. By referring to FIG. 3, stent 10 is made from a multi laminate hollow tube, or hypotube as it is often referred to by those skilled in the art, having at least two layers, wherein one layer is made from a plastically deformable material, such as stainless steel or titanium, and the inner layer is made from a superelastic material such as Nitinol. Stent 10 preferably has a stainless steel outer layer 100 and a superelastic Nitinol layer 110. The stent could have more than two layers and still possess all the advantages of the present invention. For example, the stent could be made of a superelastic material, such as Nitinol, sandwiched between two layers of a plastically deformable, such as stainless steel. The inner layer of stainless is preferably relatively thin so that the articulated sections remain elastic.

The laminate hypotube may be manufactured by any number of processes known to those skilled in the art, as evidenced in U.S. Pat. No. 5,858,566 issued on Jan. 12, 1999. In the first process the hypotube may be produced by hot rolling a series of layers of material into laminate sheets. The hot rolling process may be optimized to ensure mechanical bonding between the layers and that the composite material has the necessary tensile strength. The laminate sheets may then be rolled up around a mandrel and seam welded to form a tube. The seam welded tube can then be drawn to final size.

The second process for making the hypotube is to place multiple layers of tubes within each other around a core mandrel. The composite structure may then be drawn and heat treated using conventional wire drawing practices until the finished tube diameter meets the physical properties and dimensions required. A sacrificial ductile core mandrel is placed within the hypotube prior to the wire drawing process. The composite system is then drawn to finish dimensions and the core mandrel is removed. Removal of the mandrel is achieved by reducing the cross section of the mandrel. By solely pulling the mandrel, the diameter of the mandrel can be reduced sufficiently to be easily removed.

Once a composite hypotube is obtained, the structure may be loaded onto a lathe type tool and the slots and articulations may be cut from this tube using, for example, a laser etching cutting tool, a water saw, or an electron discharge machine. Other ways of cutting the slots, such as by photochemically etching, are well known by those of ordinary skill the art.

The present invention has an advantage in that after the stent design is cut from the tube, the articulations can then be processed so that the outer layer of stainless steel is removed from the articulations. Therefore, the articulations are now only made from the superelastic Nitinol material. This additional process is done by selective etching or laser scribing. After all etching and selective etching is complete, the tube may then be deburred by a procedure such as shot peening, abrasive tumbling, honing, electropolishing and electroetching.

By making the stent from a multi-laminate tube, wherein one layer is plastically deformable and the inner layer is superelastic, a stent having relatively rigid grafts connected by very flexible and shape recoverable articulations can be formed. This allows for a stent which is flexible enough to navigate through tortuous paths, but which is long enough to cover a relatively large target site within a vessel. As seen from FIG. 4, the stent 10 often has to pass through tight curves. FIG. 4 shows the stent 10 loaded onto a balloon catheter 120 and being navigated through a vessel 130. Because articulations 80 and 90 are made from a superelastic material, they make the stent more flexible so that it can better pass through tight curves such as the one shown here. The stent need not have the particular design shown in the figures. It could simply be a stent having a plastically deformable layer and an elastic layer, wherein the stent has elastic zones along its body where the plastically deformable layer has been removed. That is the stent could simply be a graft member having at least two layers wherein one of the layers comprises an elastic layer of material extending from end to end, and said other layer comprises a plastically deformable material covering only a predetermined portion of the elastic layer.

The multilaminate stent described herein can also be used to make a crush recoverable balloon expandable stent of the type described in U.S. patent application Ser. No. 08/735,128, filed on Oct. 22, 1996, which is hereby incorporated herein by reference. By controlling the wall thickness of the plastically deformable layer relative to the superelastic section, the performance of the device can be adjusted. For this characteristic, the wall thickness of the plastically deformable layer is targeted to plastically deform during deployment. At the same load condition, the superelastic layer is targeted to accept a load greater than the lower plateau of the stress versus strain curve for the superelastic layer and less than the upper plateau of the stress versus strain curve for the superelastic layer. In this loading condition, the radial outward force is controlled by the plastically deformable member (yield point on the stress versus strain curve) and the crush resistance is controlled by the superelastic member (upper plateau on the stress versus strain curve). This combination will develop a stent which is balloon catheter deliverable to a known stent diameter, crush resistant, and exhibits no chronic outward force.

Although particular embodiments of the present invention have been shown and described, modification may be made to the device and/or method without departing from the spirit and scope of the present invention. The terms used in describing the invention are used in their descriptive sense and not as terms of limitations.

That which is claimed is:

1. A stent for implantation into a vessel of a patient, said stent comprising;
    a) at least two plastically deformable and expandable tubular graft members for expansion within a vessel, each said graft member having a first end, a second end, a wall section disposed therebetween and a lumen extending therethrough, each of said graft members comprise stainless steel; and
    b) at least one articulation connecting the first end of one of said graft members with the second end of said other graft member, said articulation is made from a superelastic material.

2. The stent according to claim 1 wherein each expandable graft member comprises a plurality of circumferential loops, wherein adjacent loops are connected together by at least one strut.

3. The stent according to claim 1 wherein said at least one articulation comprises superelastic nickel titanium alloy.

4. The stent according to claim 1 wherein said stent has a longitudinal axis extending through said lumens of said expandable grafts, and wherein said at least one articulation connects said graft members together along a curved line which is angled with respect to said longitudinal axis.

5. A stent for implantation into a vessel of a patient, said stent comprising;
    a) at least two plastically deformable and expandable tubular graft members for expansion within a vessel, each said graft member having a first end, a second end, a wall section disposed therebetween and a lumen extending therethrough, said graft members having at least two layers wherein one of said layers comprises a plastically deformable material, and said other layer comprises a superelastic material; and
    b) at least one articulation connecting the first end of one of said graft members with the second end of said other graft member, said articulation is made from a superelastic material.

6. The stent according to claim 5 wherein each expandable graft member comprises a plurality of circumferential loops, wherein adjacent loops are connected together by at least one strut.

7. The stent according to claim 5 wherein said at least one articulation comprises superelastic nickel titanium alloy.

8. The stent according to claim 5 wherein each said plastically deformable layer of said expandable grafts comprises stainless steel, and wherein said superelastic layer of said expandable grafts comprises a superelastic nickel and titanium alloy.

9. The stent according to claim 5 wherein inner layer of said grafts are made from said superelastic material.

10. A stent for implantation into a vessel of a patient, said stent comprising: an expandable tubular graft member having a plurality of circumferential loops connected together by at least one strut, for expansion within a vessel, said graft member having a first end, a second end, a wall section disposed therebetween and a lumen extending therethrough, and wherein said graft member comprises at least two layers, wherein one of said layers comprises an elastic later of material extending from said first end to said second end, and said other layer comprises a plastically deformable material covering only a predetermined portion of said elastic layer.

11. The stent according to claim 10 wherein each said plastically deformable layer of said expandable graft comprises stainless steel, and wherein said elastic layer of said expandable graft comprises a superelastic nickel and titanium alloy.

* * * * *